US00PP11235P

United States Patent [19]

Pieters

[11] Patent Number: Plant 11,235

[45] Date of Patent: Feb. 22, 2000

[54] CHRYSANTHEMUM PLANT NAMED 'GEDI M1'

[76] Inventor: Dirk Pieters, Schierveldestraat 3A, Oosnieuwkerke, 8840 Staden, Belgium

[21] Appl. No.: 09/124,567

[22] Filed: Jul. 29, 1998

[51] Int. Cl.[7] ..... A01H 5/00

[52] U.S. Cl. ..... Plt./288

[58] Field of Search ..... Plt./288, 294

*Primary Examiner*—Howard J. Locker

*Attorney, Agent, or Firm*—Christie, Parker & Hale, LLP

[57] ABSTRACT

A new plant variety of Chrysanthemum producing small white flowers.

2 Drawing Sheets

BACKGROUND OF THE INVENTION

The present invention is directed to a new and distinct variety of Chrysanthemum plant botanically classified as *Dendranthema grandiflora*. The varietal denomination of the new chrysanthemum is 'GEDI M1'.

The female parent of the new variety is the variety known as 'Celino' and the male parent is the variety known as 'Ozenda' (U.S. Plant Pat. No. 10,419). The new variety has been asexually reproduced by vegetative cuttings in Ventura County, Calif. and the distinguishing characteristics are retained through successive generations of a sexual reproduction.

SUMMARY OF THE INVENTION

'GEDI M1' is a Chrysanthemum plant variety with white decorative/button-type flowers.

COMPARISON WITH PARENTS

'GEDI M1' has a smaller flower diameter than either parent. The new variety also has a round capitulum while 'Celino' has a flat capitulum. Flower color of 'Ozenda' is light lavender.

BRIEF DESCRIPTION OF ILLUSTRATIONS

The accompanying photographs show typical specimens of the plant and flowers of the new variety with colors being as nearly true as possible with illustrations of this type.

DESCRIPTION OF THE PLANT

Figure 1:
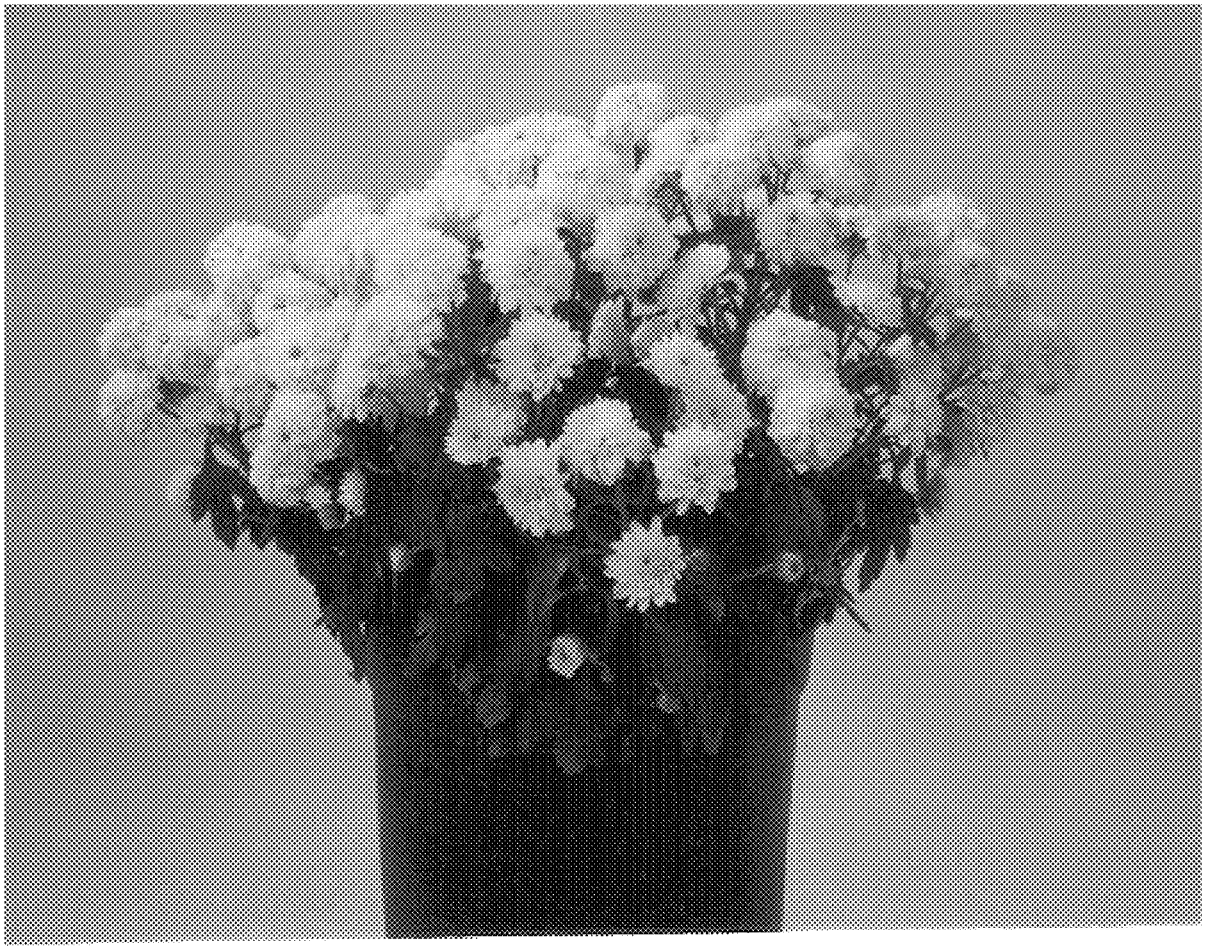
FIG. 1 is a whole plant view of the new cultivar grown in a pot.
Figure 2:
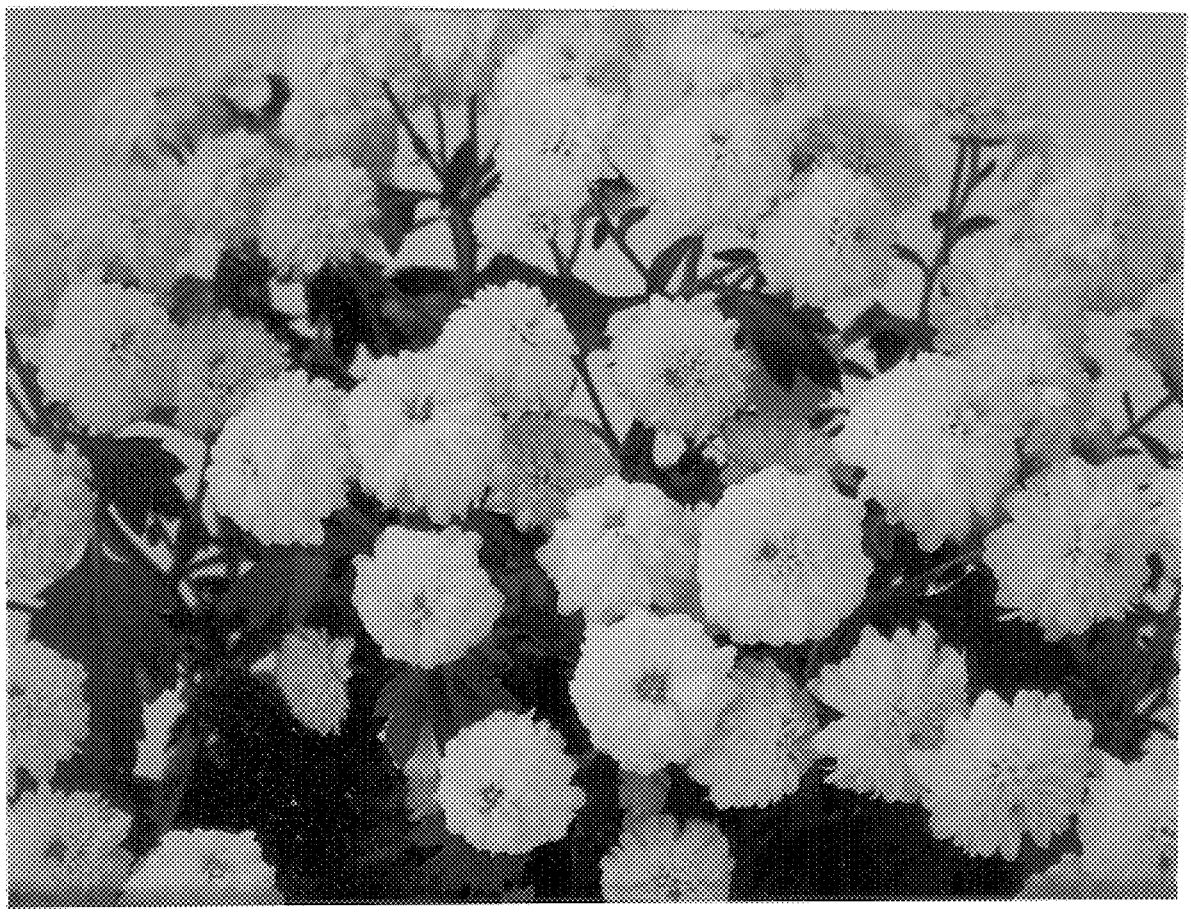
FIG. 2 is a closer view, showing inflorescence and foliage characteristics of the new cultivar in greater detail.

The following description of the new variety is of specimens grown in a greenhouse in Ventura County, Calif. in the month of April. 'GEDI M1' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'GEDI M1' is about 29 days and a response time of about 7 weeks. No treatment with growth retardant was used with plants described. Useful growing conditions include night temperatures of about 18°–20° C., day temperatures of about 20°–30° C. and about 5,000 to 6,000 foot-candles of light. The new variety is naturally blooming in September in Ventura County, Calif.

Plant:

- *Habit.*—Mounding herbaceous perennial, free branching.
- *Height.*—About 28 cm.
- *Number of breaks from pinch.*—About 4 to 5.
- *Length of lateral branches.*—About 22 cm.
- *Stem color.*—Near 138A.

Foliage:

- *Leaf arrangement.*—Alternate.
- *Number of leaves per lateral branch.*—About 15 fully expanded leaves.
- *Leaf size.*—Length: About 5.5 cm. Width: About 3.5 cm.
- *Leaf shape.*—Ovate.
- *Attachment.*—Petioled.
- *Leaf apex.*—Acute.
- *Base.*—Truncate.
- *Margin.*—Palmately lobed.
- *Aspect.*—Slightly undulate.
- *Surface.*—Top: Lightly pubescent. Bottom: Pubescent.
- *Venation.*—Prominent on underside. Color: Underside: Near 137D. Upperside: Near 146B.
- *Petiole.*—Length: About 1.3 cm. Color: Near 146B.
- *Color.*—Mature leaf. Top: Near 137B. Bottom: Near 137C. Young leaf: Top: Near 137A. Bottom: Near 137C.

Bloom:

- *Inflorescence form.*—Cyme.
- *Bloom form.*—Decorative.
- *Number of blooms per branch.*—About 8.
- *Diameter of fully expanded bloom.*—About 2.1 cm.
- *Depth of fully expanded bloom.*—About 2.1 cm.
- *Sepal number.*—About 35. Color: Near 137B.
- *Peduncle.*—Length: Uppermost: About 3.5 cm. Lateral: About 5.5 cm. Habit: Straight. Surface: Pubescent. Color: Near 138A.
- *Flower bud* (*when just showing color*).—Color: Near 155C. Diameter: About 1 cm. Height: About 0.7 cm. Shape: Flattened sphere.
- *Ray florets.*—Number per flower: About 200. Texture: Matte. Shape: Oblanceolate. Apex: 2 to 3 irregular obtuse lobes. Base: Tapered. Margin: Entire. Aspect: Strongly recurved. Length: About 1.5 cm. Width: About 0.7 cm.
- *Disc florets.*—Number per flower: About 20. Texture: Shiny. Shape: Cylindric, fluted apex. Length: About 0.6 cm. Width: About 0.1 cm.
- *Fragrance.*—Faint.

Flower color:

*General flower description.*—Small white decorative, some with slightly yellow center, some with a slight green center.

*Ray florets, top side.*—Immature: Near 155D. Mature: Near 155D. Fading: Near 155D.

*Ray floret, under side.*—Immature: Near 154D. Mature: Near 154D. Fading: Near 154D.

*Disc florets.*—Immature: Near 144C. Mature: Near 12A. Fading: Near 145C.

*Changes as the flower ages.*—White color retained. Capitulum shape becomes nearly spherical.

Reproductive organs:

*Ray florets.*—Pistillate. Stigma shape: 2 branched. Stigma color: Near 6A. Style length: About 0.5 cm. Style color: Near 154C.

*Disc florets.*—Stigma shape: Linear. Stigma color: Near 5A. Style length: About 0.3 cm. Style color: Near 4D. Stamen number: About 5.Anther length: About 0.2 cm. Pollen color: Near 13A. Pollen quantity: Moderate.

What is claimed is:

1. A new and distinct Chrysanthemum plant of the variety substantially as herein shown and described.

* * * * *